United States Patent
Chan et al.

(10) Patent No.: US 7,263,395 B2
(45) Date of Patent: Aug. 28, 2007

(54) VENOUS PULSE OXIMETRY

(75) Inventors: Fang Chiat Daniel Chan, Singapore (SG); Matthew James Hayes, Leicestershire (GB); Peter Richard Smith, Leicestershire (GB)

(73) Assignee: Loughborough University Enterprises Ltd., Leicestershire (GB)

( * ) Notice: Subject to any disclaimer, the term of this patent is extended or adjusted under 35 U.S.C. 154(b) by 53 days.

(21) Appl. No.: 10/502,758

(22) PCT Filed: Jan. 31, 2003

(86) PCT No.: PCT/GB03/00427

§ 371 (c)(1),
(2), (4) Date: May 3, 2005

(87) PCT Pub. No.: WO03/063697

PCT Pub. Date: Aug. 7, 2003

(65) Prior Publication Data

US 2005/0256386 A1    Nov. 17, 2005

(30) Foreign Application Priority Data

Jan. 31, 2002  (EP)  .................................. 02250689
Jan. 31, 2002  (GB)  .................................. 0202285.3

(51) Int. Cl.
*A61B 5/00*    (2006.01)

(52) U.S. Cl. ...................................................... 600/335
(58) Field of Classification Search ................ 600/310, 600/322, 323, 335
See application file for complete search history.

(56) References Cited

U.S. PATENT DOCUMENTS

| 4,927,264 A | 5/1990 | Shiga et al. |
| 5,638,816 A | 6/1997 | Kiani-Azarbayjany et al. |
| 6,018,673 A | 1/2000 | Chin et al. |
| 6,213,952 B1 | 4/2001 | Finarov et al. |
| 6,222,189 B1 * | 4/2001 | Misner et al. .............. 600/335 |

FOREIGN PATENT DOCUMENTS

WO    WO99 62399 A    12/1999

* cited by examiner

*Primary Examiner*—Eric F. Winakur
(74) *Attorney, Agent, or Firm*—Nixon & Vanderhye

(57) ABSTRACT

A method of non-invasively measuring venous oxygen saturation, comprising: applying a pressure transducer at a first site on a body, applying a drive signal to the external pressure transducer at a predetermined frequency, to cause a series of pulsations of a predetermined magnitude in the venous blood volume in the vicinity of said first site, applying an oximeter device at a second site on the body, measuring output signals received from said oximeter device, said output signals containing a component representative of the modulation of venous blood volume due to said pulsations, deriving a measure of venous oxygen saturation from the frequency response of said output signals.

18 Claims, 8 Drawing Sheets

Desaturation Experiment

Modulation frequency at 4Hz and modulation depth at 160mmHg

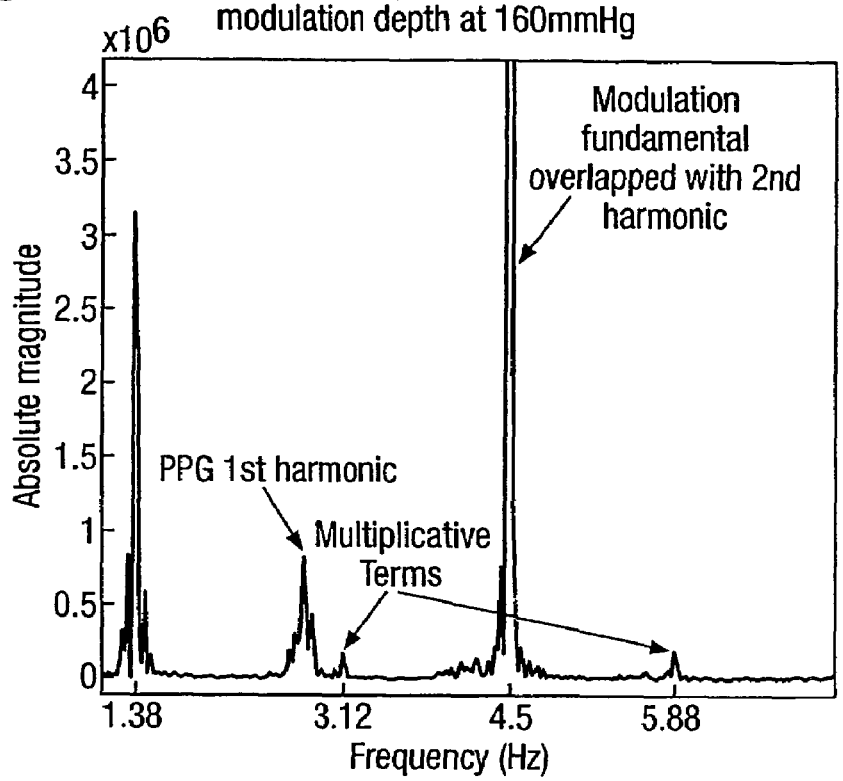
Fig.7b. Modulation frequency at 4.5Hz and modulation depth at 160mmHg
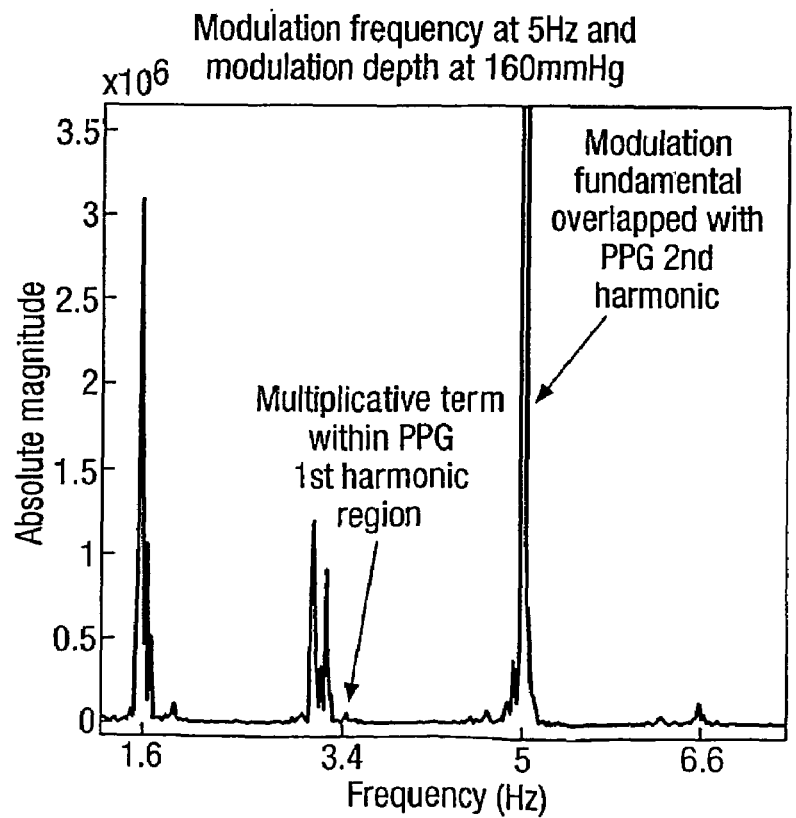
Fig.7c. Modulation frequency at 5Hz and modulation depth at 160mmHg

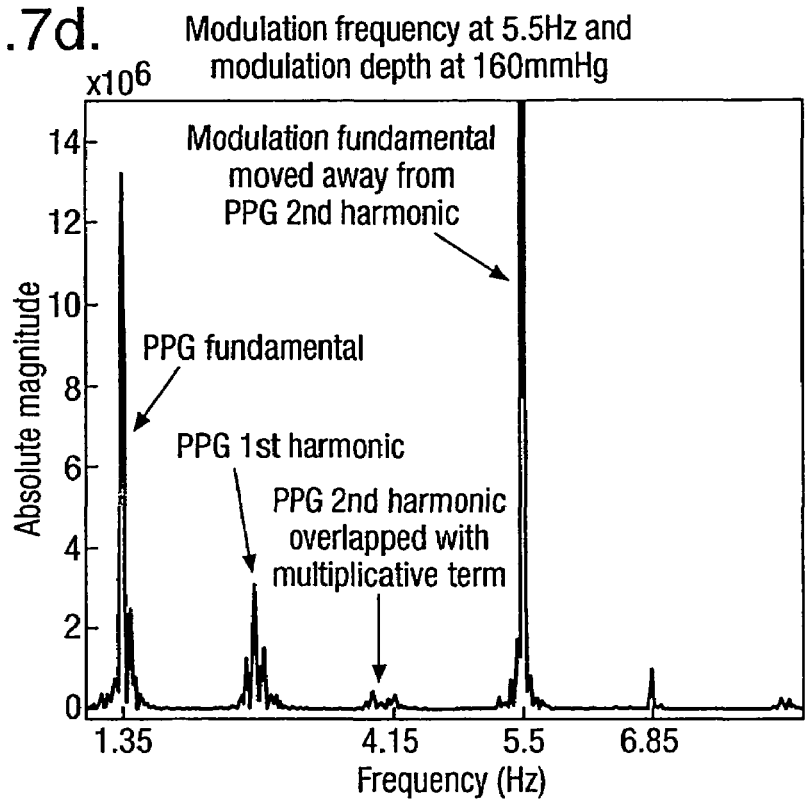
Fig.7d. Modulation frequency at 5.5Hz and modulation depth at 160mmHg
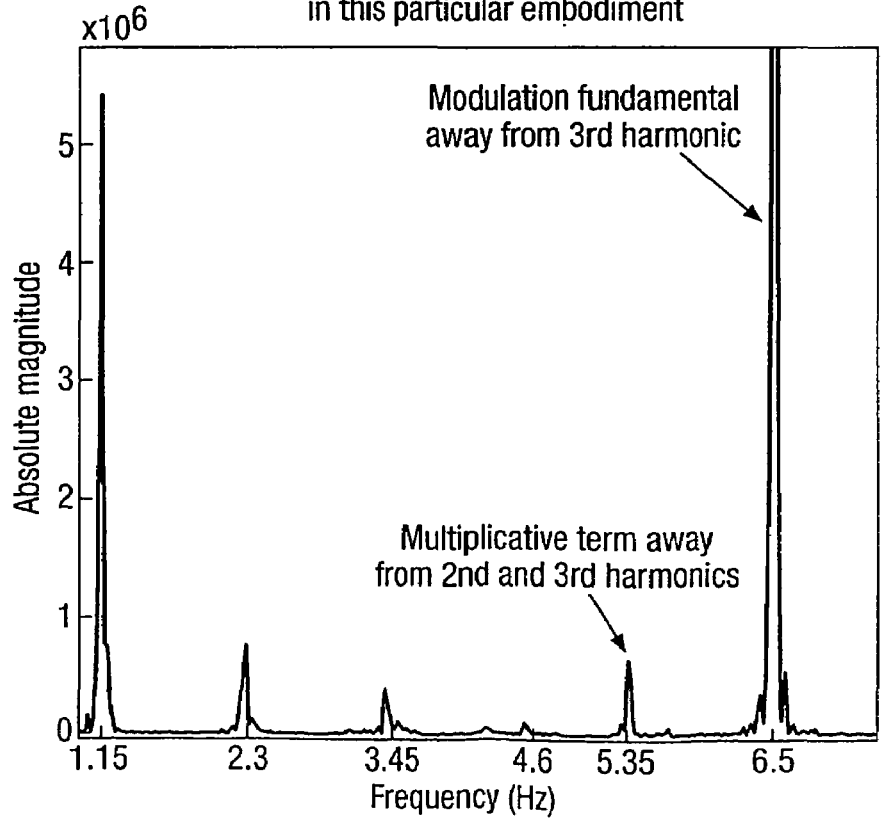
Fig.7e. Optimisted modulation frequency in this particular embodiment

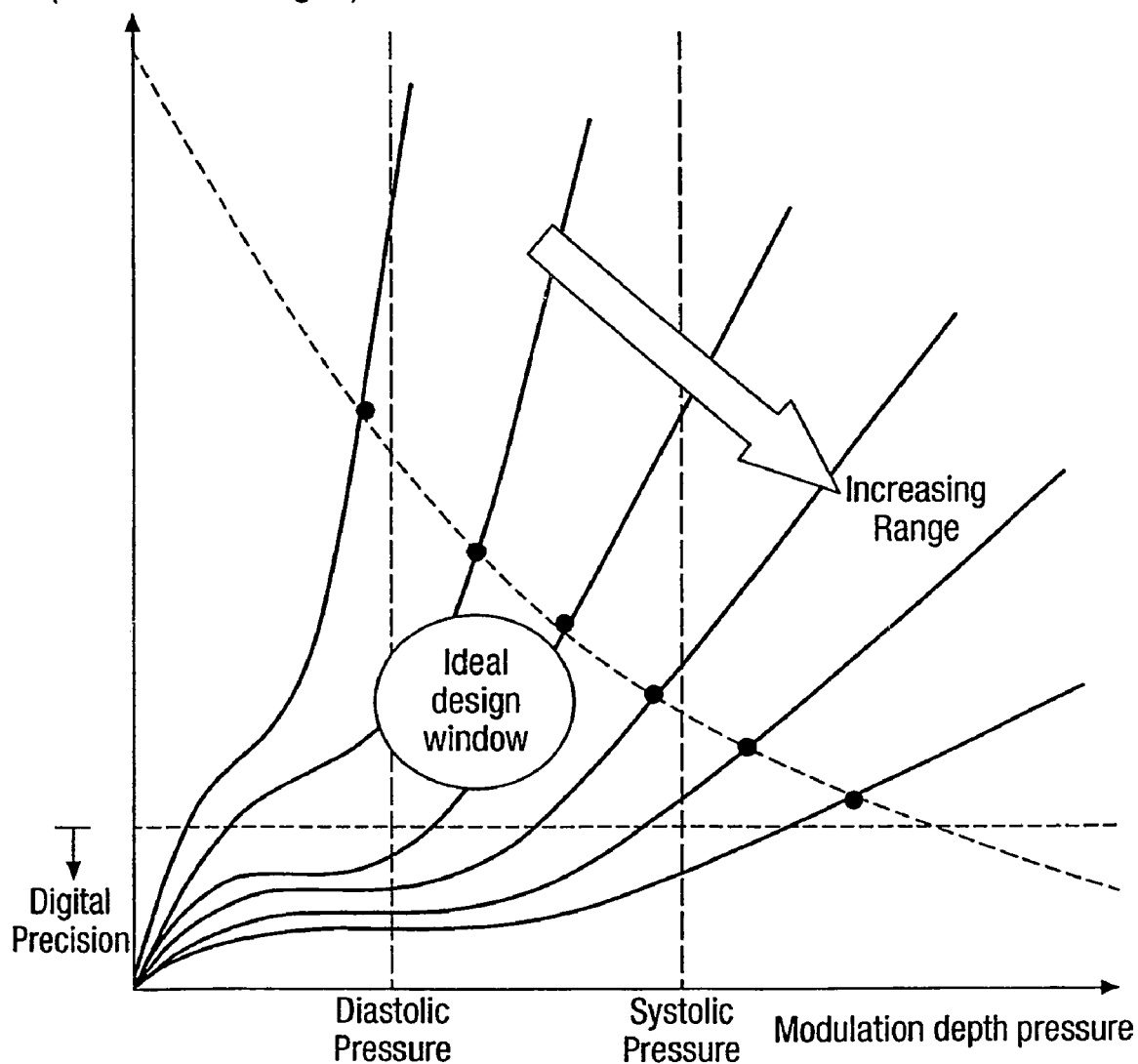

VENOUS PULSE OXIMETRY

This application is the U.S. National Phase of International Application PCT/GB03/00427, filed 31 Jan. 2003, which designated the U.S.

FIELD OF THE INVENTION

This invention relates to a means of inducing regular modulations of the venous blood volume and the associated measurement of those modulations using sensors. By illuminating vascular tissue and detecting the light that has passed through the tissue, changes in blood volume due to differential absorption of the light intensity can be registered. This finds particular application in the measurement of venous blood oxygen saturation, achieved by the use of at least two separate wavelengths of illumination and subsequent detection.

BACKGROUND OF THE INVENTION

The monitoring of venous blood oxygen saturation ($SvO_2$) is called venous oximetry. The method is often used in Intensive Care Units (ICU) to monitor the patient's overall oxygen supply and consumption. Current invasive methods have resulted in its under-utilization although $SvO_2$ is unquestionably a valuable assessment tool in the evaluation of oxygenation.

All venous oximetry techniques can be categorised into two areas, methods that are invasive and those that are non-invasive. A discussion of the various known invasive and non-invasive techniques follows.

Oxygen saturation can be measured invasively by employing a variation of the standard Swan-Ganz Pulmonary Artery Catheter (PAC) in which two fiberoptic bundles were inserted in the PAC. The modified PAC used the principle of reflection spectrophotometry to make quantitative measurement of oxygen transport. Due to its invasive nature and the cost of the modified PAC, the method is not employed extensively for venous oximetry. U.S. Pat. No. 5,673,694 is representative of this background art.

The majority of non-invasive, continuous peripheral venous oximetry techniques are based on Near InfraRed Spectroscopy (NIRS) or a combination of NIRS and various exercise protocols such as over-systolic venous occlusion. NIRS is hindered from supplanting the current invasive, continuous method utilizing $SvO_2$ or central venous catheter mainly due to the difficulty in determining certain critical parameters without which calibration for venous oximetry would not be possible. Prior art approaches based upon NIPS are disclosed in U.S. Pat. Nos. 6,015,969 and 5,661,302.

Pulse oximetry is one of the main applications of photoplethysmography (PPG), and is widely used for the measurement of arterial oxygen saturation, $SpO_2$. The PPG waveform contains two components, one which is attributable to the pulsatile component in the vessels, i.e. the arterial pulse, is caused by the heartbeat and gives a rapidly alternating signal (AC component), and the other is due to the blood volume and its change in the skin and gives a steady signal that only changes slowly (DC component).

Two wavelengths of light are used in Pulse oximetry, one in the red band (660 nm) and one in the infrared band (940 nm). Since at 660 nm reduced hemoglobin absorbs more light than oxyhemoglobin and at 940 nm, oxyhemoglobin absorbs more light than its reduced form, pulse oximetry relates this differential measurement to the arterial oxygen saturation.

In pulse oximetry, light is first being transmitted through the tissues and the intensity of the transmitted light is then measured by a photo detector on the other side. The pulse oximeter first determines the AC component of the absorbance at each wavelength and then divides it by the corresponding DC component to obtain ratio that is independent of the incident light intensity. The ratio of ratios is then constructed as:

$$R = \frac{AC_{660}/DC_{660}}{AC_{940}/DC_{940}}$$

The pulse oximeter is then calibrated by measuring the ratio of ratios and simultaneously sampling arterial blood for in vitro saturation measurements.

Whilst the use of these techniques is effective for the measurement of arterial blood oxygen saturation, it relies upon the presence of pulsations of the arterial blood which is generated by the heart. No such measurable pulsations are present in venous blood.

Venous Occlusion Plethymography (VOP) is the measurement of changes in tissue volume in response to temporary obstruction of venous return. It is used clinically to measure certain physiological conditions of blood vessels such as venous capacitance. VOP relies on the principle that occlusion of venous return causes slight swelling of distal portion of the tissue under test due to continued arterial inflow. The step response of venous blood volume over time during VOP can be used to measure arterial blood flow, venous outflow and venous compliance.

M. Nitzal et al (Journal of Biomedical Optics 5(2), 155-162, April 2000) employed the principle of VOP to the measurement of $SvO_2$, by applying pressure to the forearm sufficient to completely occlude venous flow, but leave arterial flow unaffected. Light absorption at 2 wavelengths is compared before and after occlusion. However, the approach does not appear to yield separate determination of venous and arterial oxygen saturation.

PCT publication WO99/62399 and U.S. Pat. No. 5,638,816 relate to methods of venous oximetry where a cyclical active pulse is applied via an external cuff. However, the level of modulation (10% of the DC signal) is large, and will require a cuff-sensor spacing so close that the optical coupling will be affected, or if further away, pulsations will be at a level which will cause perturbations in the arterial system, and hence lead to inaccuracies in venous oxygen saturation measurements.

As indicated above, prior art techniques for measuring venous oxygen saturation by non-invasive means do not yield the requisite accuracy. The aim of the invention is to achieve an improved measure of venous oxygen saturation.

The principles of arterial pulse oximetry are well known (see above). The crucial element of the method that enables specific calibration of the oxygen carrying hemoglobin depends upon the presence of blood volume pulsations in the arterial system. These pulsations are of course naturally present throughout the circulation system. If one could induce pulsations in the venous system and properly isolate them from those of the arterial system, a similar calibration method could be employed to measure venous oxygen saturation.

According to the invention, there is provided a method of non-invasively measuring venous oxygen saturation, comprising applying a pressure transducer at a first site on a body, applying a drive signal to the external pressure transducer at a predetermined frequency, to cause a series of pulsations of a predetermined magnitude in the venous blood volume in the vicinity of said first site, applying an oximeter device at a second site on the body, measuring output signals received from said oximeter device, said output signals containing a component representative of the modulation of venous blood volume due to said pulsations, deriving a measure of venous oxygen saturation from the frequency response of said output signals.

The term oximeter device is intended to encompass any device which uses light of different frequencies to determine tissue oxygen content. It may encompass both transmission and reflection mode devices.

The relationship between the distance between the first and second sites on the one hand, and the magnitude of the pulsations on the other hand, may be arranged such that a multiplicative term in the frequency spectrum of the measured signals, indicative of a disturbance to the arterial system, is minimised.

Preferably the frequency of the drive signal is chosen such that the pulsations are distinguishable from the heart rate.

The relationship between the frequency $\omega_m$ of the pulsations caused by said drive signal and the heart rate $\omega_{HR}$ can be chosen to comply with the following conditions:

$$\omega_m \neq n(\omega_{HR} \pm \Delta\omega_{HR})$$

and $$\omega_m \pm (\omega_{HR} \pm \Delta\omega_{HR}) \neq n(\omega_{HR} \pm \Delta\omega_{HR})$$

where n>1

The frequency of the drive signal can be determined iteratively on the basis of a real time measurement of the heart rate.

Ideally the magnitude of the pulsations is controlled such that the venous blood system is modulated without disturbing the arterial system. The magnitude of the pulsations can be controlled such as to cause a variation of less than 1% in the DC level of the received signal, or more preferably a variation of approximately 0.1% in the DC level of the received signal.

In an alternative embodiment the oximeter is placed on a digit and a further pressure transducer is placed away from a distal end of a limb, and arranged to occlude the supply of blood to and from said limb, and the measurement is performed during the period of occlusion.

Advantageously, the optimum magnitude of the pulsations can be determined by progressively increasing the pulsation magnitude and observing a frequency response of the output signals; the appearance of a multiplicative term in the frequency spectrum being indicative of the maximum permissible magnitude having been reached. Upon reaching the point where a multiplicative term appears, the pulsation magnitude can be subsequently reduced to a point where the multiplicative term becomes insignificant.

The method may further include a calibration step, during which the spacing between the first and second sites is varied while the pulsation magnitude is held constant, in order to derive an optimum spacing. The calibration step may include a further step of varying the pulsation magnitude while the spacing of the first and second sites is held constant.

In a further embodiment the method may include the measurement of arterial oxygen saturation derived from the frequency response of the output signals, such that the difference in levels of the arterial and venous oxygen saturation being representative of tissue oxygen consumption.

The invention also provides an apparatus for non-invasively measuring venous oxygen saturation comprising a pressure transducer for applying a series of pulsations to a first site on a body, a pulse oximeter, control means for controlling the frequency and/or magnitude of said pulsations, such that the venous blood volume is modulated, signal processing means for extracting a value for venous oxygen saturation from signals received from said oximeter, said signals containing a component representative of a modulation of venous blood volume due to said pulsations.

Advantageously, the control means operates to control the relationship between the frequency $\omega_m$ of the pulsations caused by said drive signal and the heart rate $\omega_{HR}$ according to the following conditions:

$$\omega_m \neq n(\omega_{HR} \pm \Delta\omega_{HR})$$

and $$\omega_m \pm (\omega_{HR} \pm \Delta\omega_{HR}) \neq n(\omega_{HR} \pm \Delta\omega_{HR})$$

where>1

Preferably the pressure transducer comprises an inflatable digit cuff supplied with air from an air pump; the pressure transducer and the pulse oximeter may be formed as an integral device.

In order that the invention may be more fully understood an embodiment thereof will now be described by way of example with reference to the accompanying drawings in which:

FIGS. 7a to 7e show graphs of the effect of variation of the modulation frequency on the power spectrum of the received signals from the oximeter device.

FIG. 8 shows the relationship between the received signal amplitude and the modulation pressure for a range of cuff to oximeter probe spacings.

Figure 1:
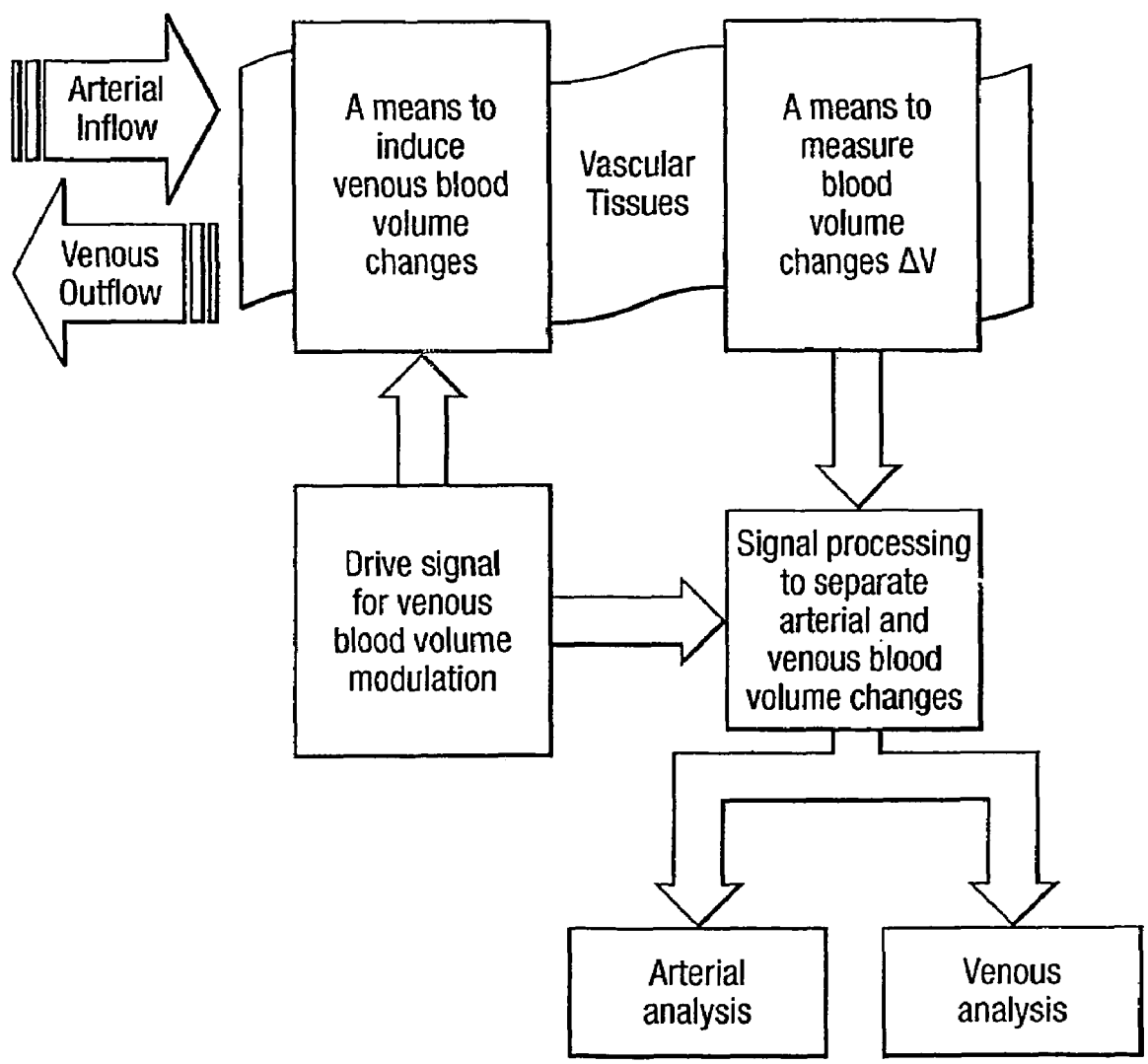
FIG. 1 illustrates the general principle by which the invention operates.

With reference to FIG. 1, the principle of the invention will now be described. In its simplest form, the invention involves some means for inducing changes in venous blood volume and a corresponding means for measuring the changes induced. The signals extracted are processed to yield at least a separate value for venous oxygen saturation, and where necessary, a value for arterial oxygen saturation.

The generalized theory underlying the invention will now be explained. Extending the lowest order conventional description of arterial pulse oximetry can make a zeroth order theoretical description of venous pulse oximetry. The Beer-Lambert law, which couples physical path length and effective absorbance into a single definition of optical density, is commonly used in arterial pulse oximetry to assign physical significance to changes in the optical path length. According to this model, we can write the received intensity due to a particular illuminating wavelength, $\lambda$, in terms of the proportion of arterial hemoglobin that is chemically combined with oxygen, S, $$I(t,\lambda) = I_0(\lambda) \exp\{-[S\epsilon_{HbO_2}(\lambda) + (1-S)\epsilon_{Hb}(\lambda)]z(t) - \mu_{static}d\}, \quad (1)$$

where $\epsilon_{HbO_2}(\lambda)$, $\epsilon_{Hb}(\lambda)$ are the millimolar extinction coefficients of oxygenated and de-oxygenated hemoglobin respectively, z(t) is a function of both the dynamic physical path length through arterial blood and the total hemoglobin concentration, and $\mu_{static}d$ is the optical density of the non-pulsatile tissue and other anatomical components.

By distinguishing optical paths through venous $z_v(t)$ and arterial $z_a(t)$ blood we may generalize the model equation (1) to $$I(t,\lambda) = I_0(\lambda) \exp\{-\mu_a z_a(t) - \mu_v z_v(t) - \mu_{static}d\}, \quad (2)$$

where we have made the substitutions $$\mu_a(\lambda) = [S_a \epsilon_{HbO_2}(\lambda) + (1-S_a)\epsilon_{Hb}(\lambda)]$$

$$\mu_v(\lambda) = [S_v \epsilon_{HbO_2}(\lambda) + (1-S_v)\epsilon_{Hb}(\lambda)]$$

We now explore small changes in the received intensity resulting from small changes in the optical paths (resulting from the presence of low amplitude venous and arterial modulations) and consider the resultant changes (AC) normalized by the quasi-static (DC) intensity, namely $$\frac{\Delta I(t, \lambda)}{I(t, \lambda)} \cong -\mu_a \Delta z_a(t) - \mu_v \Delta z_v(t). \quad (3)$$

The quantities expressed in equation (3) can be separated by electronic (or other signal processing methods) since the induced venous modulations are of known origin. One method of separation is to induce a frequency modulation of the venous system in a band that is distinct from the arterial pulsations. Once isolation of the arterial and venous dynamics is achieved the process of calibration can be applied. Inversion of the classical Beer-Lambert model of pulse oximetry is usually achieved by generating two instances of equation (3) at two different wavelengths. These equations are then solved for a quantity known as the ratio of ratios, R, which is defined as the ratio of the total extinction of blood at the two wavelengths used. Assuming each term in equation (3) has been isolated, we may form two "ratio of ratios":

$$R_a = \left[\frac{I(t, \lambda_2)\Delta I(t, \lambda_1)}{I(t, \lambda_1)\Delta I(t, \lambda_2)}\right]_a = \frac{\mu_a(\lambda_1)}{\mu_a(\lambda_2)} \quad (4)$$

$$R_v = \left[\frac{I(t, \lambda_2)\Delta I(t, \lambda_1)}{I(t, \lambda_1)\Delta I(t, \lambda_2)}\right]_v = \frac{\mu_v(\lambda_1)}{\mu_v(\lambda_2)}.$$

Knowledge of the extinction coefficients of oxygenated and deoxygenated hemoglobin at the two wavelengths can then be used to estimate $S_a, S_v$ from the calculated R using the formulae $$S_a = \frac{R_a \varepsilon_{Hb}(\lambda_2) - \varepsilon_{Hb}(\lambda_1)}{R_a[\varepsilon_{Hb}(\lambda_2) - \varepsilon_{HbO_2}(\lambda_2)] - [\varepsilon_{Hb}(\lambda_1) - \varepsilon_{HbO_2}(\lambda_1)]} \quad (5)$$

$$S_v = \frac{R_v \varepsilon_{Hb}(\lambda_2) - \varepsilon_{Hb}(\lambda_1)}{R_v[\varepsilon_{Hb}(\lambda_2) - \varepsilon_{HbO_2}(\lambda_2)] - [\varepsilon_{Hb}(\lambda_1) - \varepsilon_{HbO_2}(\lambda_1)]}$$

The invention will now be illustrated by way of example by description of a specific embodiment, involving the modulation of venous blood volume in the index finger to thereby inject a pulsatile signal into the venous blood. The methods of achieving the modulation, recording of the signal and extraction of the modulated signal will be outlined below.

A digit cuff measuring 90 mm long and 16 mm wide was obtained from Hokanson®. Modulation of the venous blood volume within the index finger is achieved by continuously inflating and deflating the digit cuff which is wrapped around the base of the index finger. The high modulating frequency (six to seven Hertz) can be achieved mainly because the volume of air needed to inflate the digit cuff in order to cause a partial occlusion of the digit and hence a significant fractional blood volume change is small. In the same way, the time to deflate the cuff is short as the volume of air within the cuff is small.

A micro pressure air pump from Sensidyne® was obtained as an air source for the digit cuff. It is able to maintain an air flow of 6.1 LPM and a minimum pressure of 4.9 psig. These specifications are suitable for the application of inflating the digit cuff to a suitable pressure in order to cause a significant fractional blood volume change and cause a pulsatile signal that is comparable to the arterial pulsation.

A solenoid operated pinch valve was obtained from BioChem Valve® in order to modulate the digit cuff. The three-way pinch valve has one normally closed valve and one normally open valve. When the solenoid is energised, the configuration changes over. One valve is used to control the tube leading from the micro air pump to the digit cuff and the other is used to control the outlet from the digit cuff. During inflation, the tube leading from the micro air pump is opened in order to allow air to enter the digit cuff and the tube that is used as an air outlet from the digit cuff is closed. During deflation, the tube leading from the air pump into the digit cuff is 'pinched' and therefore closed and at the same time the tube leading from the digit cuff which is used as an air outlet is opened to allow air within the digit cuff to escape. By controlling the three-way pinch valve, modulation of the digit cuff at a certain frequency can be achieved.

The new method of non-invasive venous oximetry works in conjunction with a standard pulse oximeter finger probe attached to a PPG system. The digit cuff is wrapped around the base of the index finger and the finger probe is also mounted to record the modulated venous blood volume signal. The probe to cuff spacing is selected to yield a suitable level of modulation in the received signal, as will be discussed in more detail later in this specification. As the finger probe used comes equipped with two light sources, red and infrared, two different signals of the modulated venous blood volume are recorded. These signals are in turn used to formulate the ratio of ratios which is related to the oxygen saturation of the venous blood ($SvO_2$).

The recorded signal will consist of two signals of different frequencies. One signal is the PPG signal that is related to the arterial pulsation which frequency is the subject's heart rate. The second signal is the modulated venous blood volume signal, that may be modulated at a frequency set away from the arterial pulsation so as to aid extraction of it through filtering techniques.

Figure 2A:
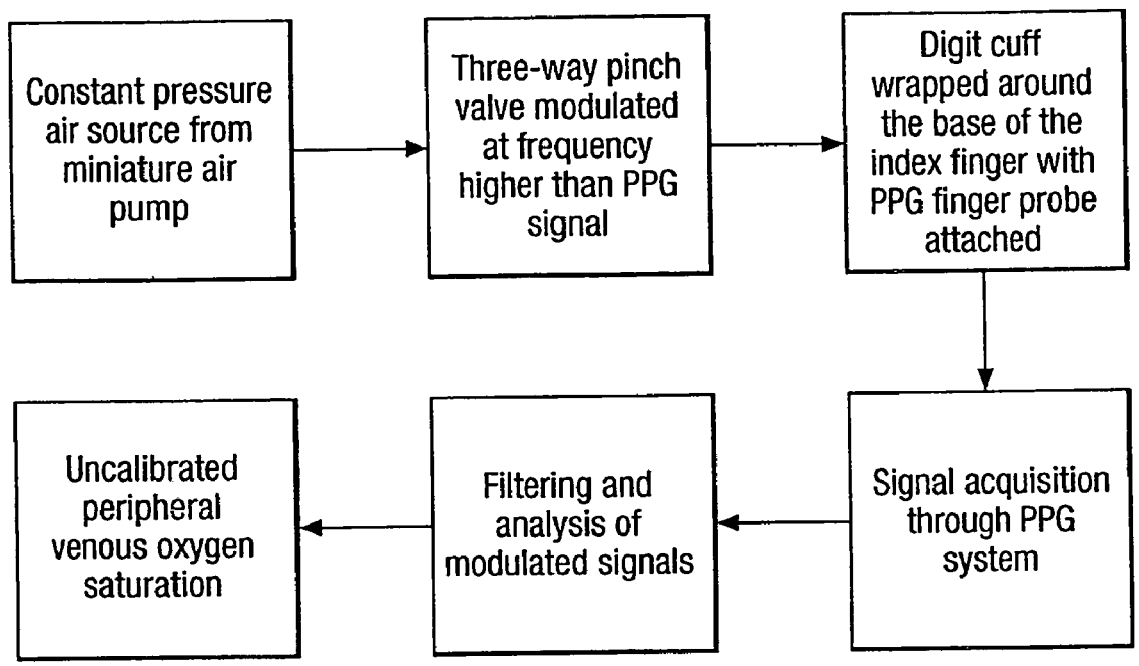
FIG. 2 shows a block diagram of the operation of an embodiment of the invention.
Figure 2B:
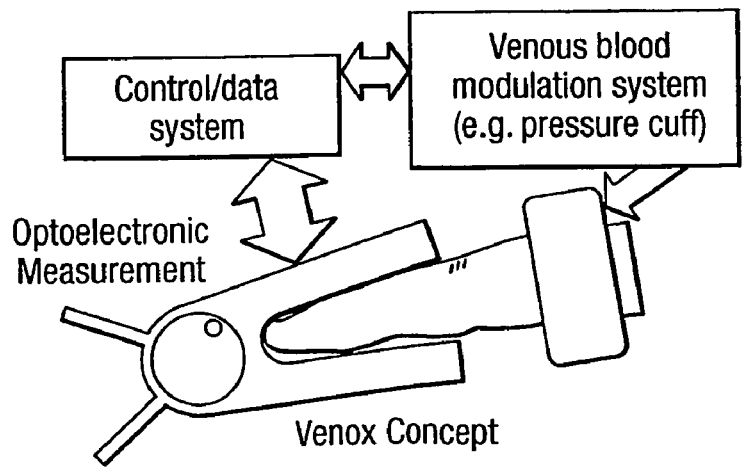

FIG. 2 illustrates the operation of this embodiment in schematic form. A discussion of the results obtained with this embodiment now follows.

Figure 3:
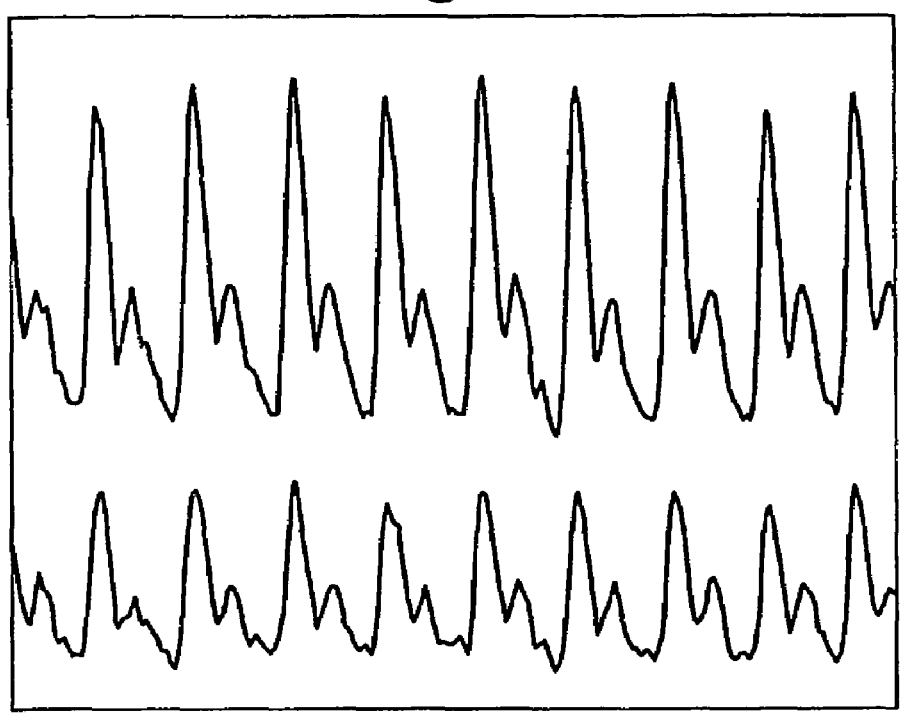
FIG. 3 shows an example of output waveforms from the oximeter device without venous blood volume modulation.

The diagram in FIG. 3 shows the PPG signals (AC components) recorded without any venous blood volume modulation. The signal sources used to obtain the top waveform and bottom waveform were IR and Red respectively.

Figure 4:
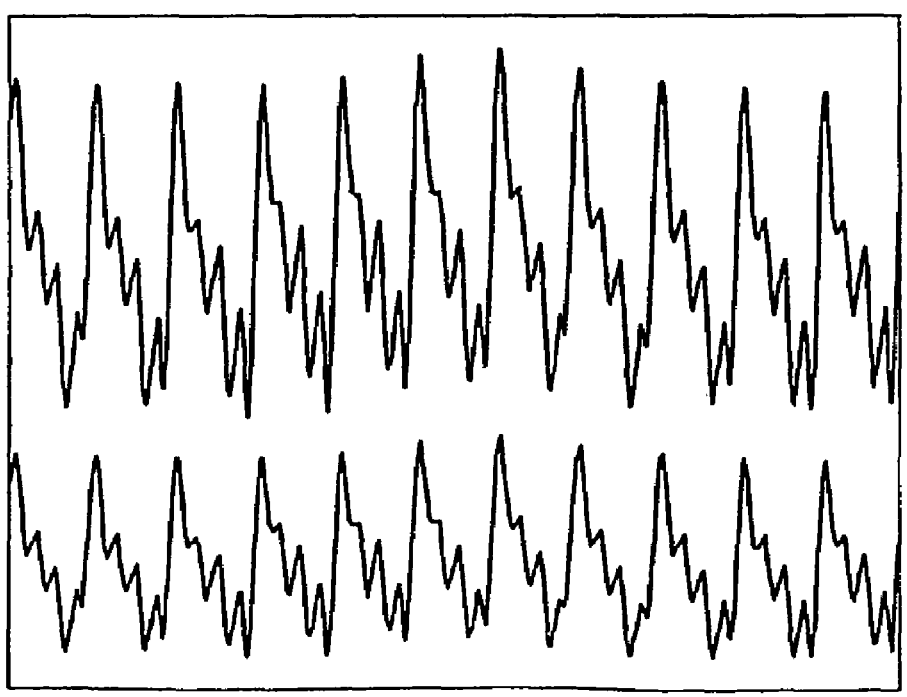
FIG. 4 shows the waveforms generated according to the invention.

The diagram in FIG. 4 shows the waveforms that were recorded when the venous blood volume was modulated at a frequency higher than the PPG signal and at a pressure that was below systole.

Figure 5:
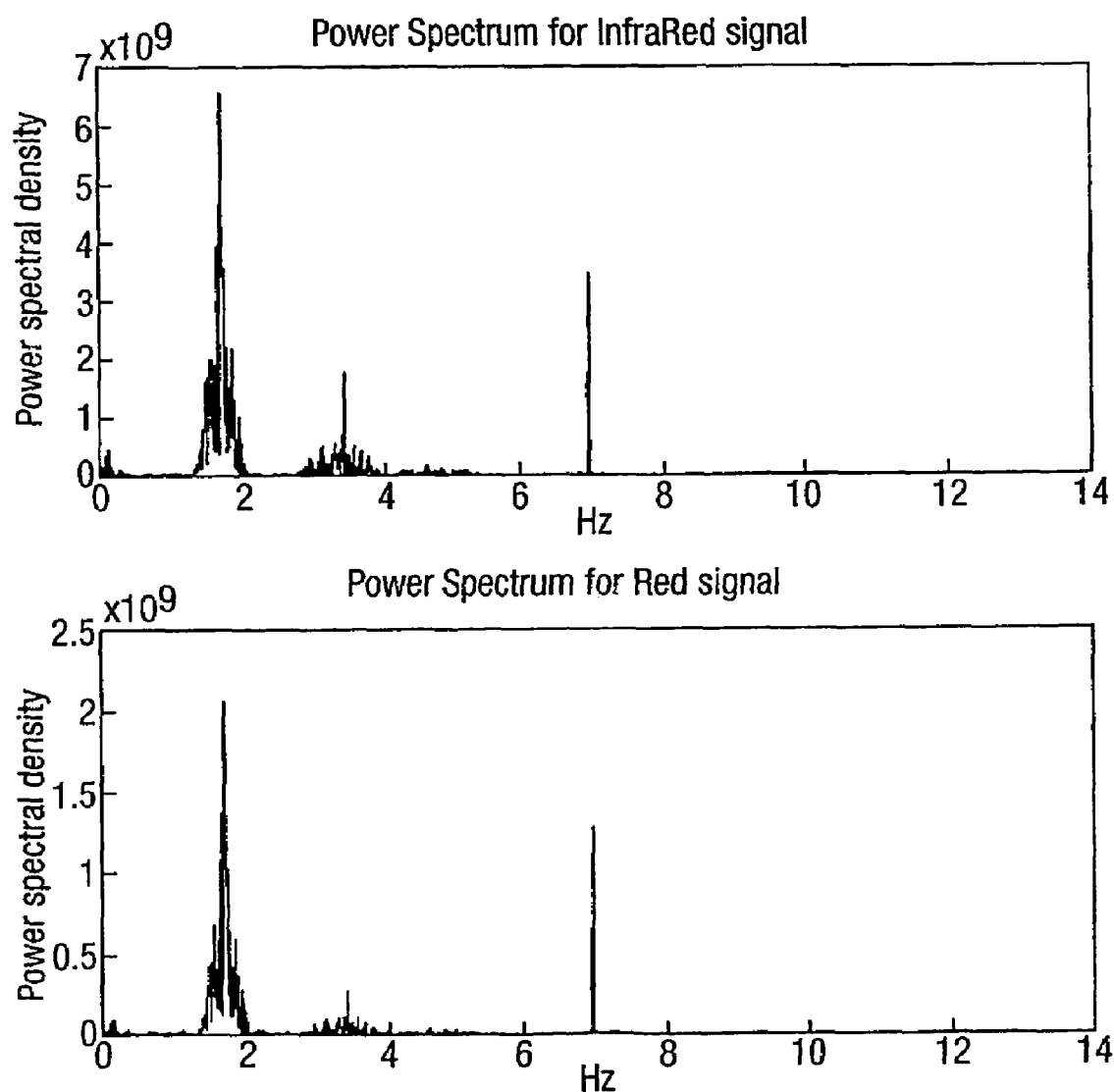
FIG. 5 shows the frequency spectrum at the two frequencies of the PPG signals.

By performing a Fast Fourier Transform (FFT) on the modulated waveforms, the power spectrum density of the two wavelengths can be obtained. FIG. 5 shows the power spectrum density at the two wavelengths.

It can be seen from the power spectrums that the modulation of venous blood was at seven Hertz and at a pressure lower than the systolic pressure. The modulated venous blood volume can be easily extracted through band-pass filtering method and the ratio of ratios can be formulated in the same way as described earlier in the background discussion of the pulse oximeter. This can then be calibrated in the same manner with measurement of the oxygen saturation of blood samples by co-oximeter drawn from the pulmonary artery. In this way, a non-invasive mixed venous blood oximetry can be achieved.

Figure 6:
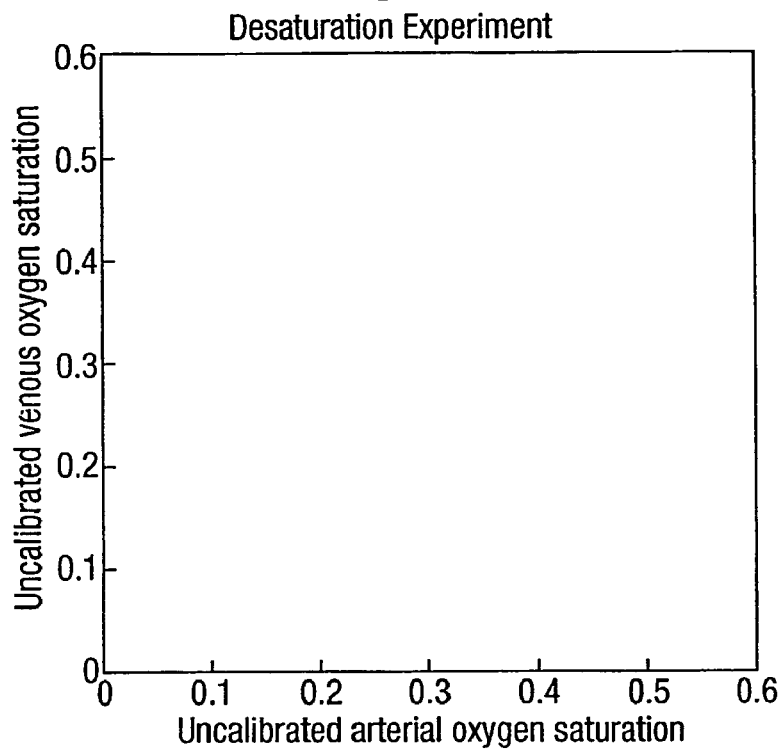
FIG. 6 illustrates the correlation between the arterial blood oxygen saturation and the venous oxygen saturation.

A preliminary calibration of uncalibrated $SaO_2$ to uncalibrated $SvO_2$ is shown in FIG. 6. The graph clearly shows a correlation between arterial oxygen saturation and venous oxygen saturation.

As mentioned above, it is important that the signal due to modulation of the venous blood can be separated from the PPG signal. One way of achieving this is to ensure that the frequency with which the pulsations are applied is chosen such that is distinct from the PPG signal.

In order to optimise the modulation frequency, both the modulation fundamental frequency and the multiplicative term if any should be set away from the second harmonic of the PPG signal. The frequency of the multiplicative term not only depends on the modulation frequency but also on the PPG fundamental frequency, that is, the heart rate. Since the normal heart rate at rest can vary, an optimisation phase can be introduced just before any actual measurement during operation. The purpose of the optimisation phase is to first gauge the heart rate of the subject and then position the modulation frequency in such a way that both the $1^{st}$ and $2^{nd}$ harmonics of the PPG signal are not obscured by the modulation fundamental frequency or the multiplicative term.

An optimisation phase may be needed since the variability of the heart rate and the perceived modulation depth at the measurement site depends on the physiological profile of the subject.

The upper limit of the modulation frequency is a function of the frequency response of the vascular system. Therefore too high a modulation frequency will cause the modulating signal to fail to register completely.

During this optimisation phase, the modulation depth can be adjusted according to the magnitude of the multiplicative term, as will be described in more detail later. In this way both the modulation frequency and modulation depth could be optimised before any actual measurement during operation. The optimisation phase can also be made adaptable throughout the operation, so that real time changes in heart rate could be compensated for by adapting the modulation frequency to the changes.

There are two conditions that need to be satisfied during modulation frequency optimnisation. In order to illustrate these two conditions, it helps to use a mathematical model each to represent the PPG signal and the modulating signal.

The PPG signal can be represented by the equation:

$$f_{HR}(t) = \sum_{n=1} f_n \sin(n\omega_{HR}t + \phi_{HR}) \qquad (1)$$

Where $f_n$ is the coefficient and $\omega_{HR}$ is the PPG fundamental frequency and n represent the harmonics (n=1 is the fundamental frequency), and $\phi_{HR}$ is the phase involved.

The modulating signal can be represented by the equation:

$$f_m(t) = g_0 \sin(\omega_m t + \phi_m) \qquad (2)$$

Where $g_0$ is the coefficient $\omega_m$ is the modulation frequency and $\phi_m$ is the phase in the model.

To illustrate the variability of the heart rate the equation (1) can be rewritten as:

$$f_{HR}(t) = \sum_{n=1} f_n \sin(n(\omega_{HR} \pm \Delta\omega_{HR})t + \phi_{HR}) \qquad (3)$$

The two conditions which need to be met for optimisation of the measurement are:

$$\omega_m \neq n(\omega_{HR} \pm \Delta\omega_{HR}) \qquad (4)$$

and $$\omega_m \pm (\omega_{HR} \pm \Delta\omega_{HR}) \neq n(\omega_{HR} \pm \Delta\omega_{HR}) \qquad (5)$$

where n>1

In this way, a table can be constructed to identify the forbidden frequencies. Assuming a heart rate is 70 and the variability is ±10

| Forbidden frequency bands | |
|---|---|
| $\omega_m$ for condition at (4) | $\omega_m$ for condition at (5) |
| 2 Hz to 2.7 Hz | 1 Hz to 4 Hz |
| 3 Hz to 4.05 Hz | 2 Hz to 2.7 Hz |

Therefore $\omega_m$ should be at least greater than 4 Hz but less than the filter upper cut-off frequency for signal detection (typically 3 Hz to 6 Hz). Most commercial $SpO_2$ devices use low cut-off frequencies. Thus $\omega_m$ must be set in a narrow range of optimised band.

The graphs shown in FIGS. 7a to 7e are the power spectrums of the PPG signal with venous modulation at various frequencies. A relatively high modulation depth of 160 mmHg was chosen such that the multiplicative term could be significantly registered.

Figure 7A:
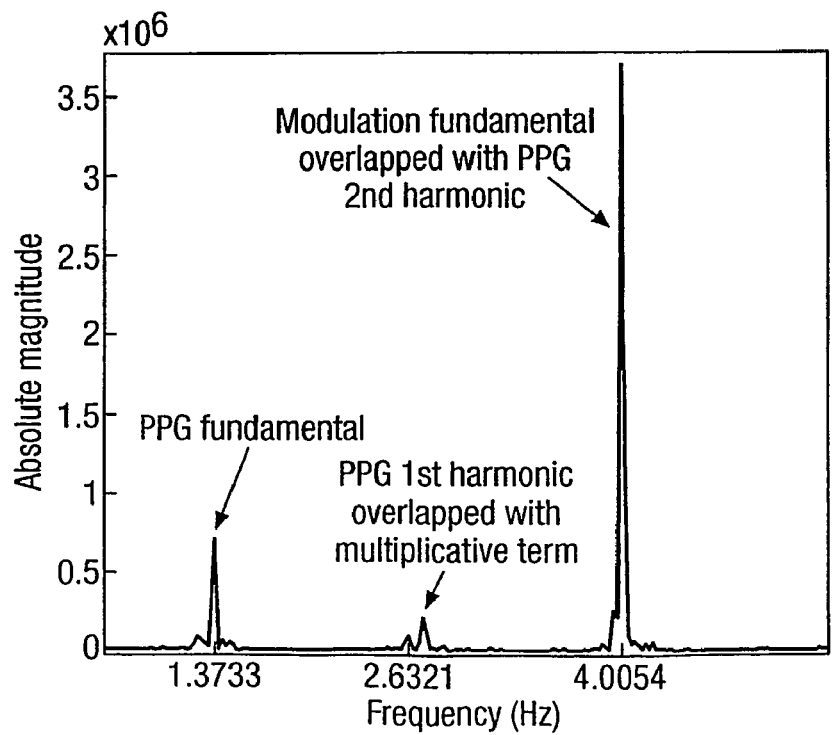

In the first graph shown in FIG. 7a, the first harmonic (n=2) of the PPG signal overlapped with the multiplicative term and the modulation fundamental overlapped with the $2^{nd}$ harmonic. Thus the modulation frequency of 4 Hz failed both the conditions. This would pose a problem when it comes to spectrally separating the two signals. Furthermore, in optimising the modulation depth, the magnitude of the multiplicative term is important in determining the degree of coupling between the two signals, the overlapping of the multiplicative terms with PPG harmonics would cause erroneous measurement of the magnitude.

In the second graph (FIG. 7b), at 4.5 Hz, the multiplicative term started to move away from the first harmonic but the modulation frequency remained dangerously close to the $2^{nd}$ harmonic.

The third graph illustrates the situation when the heart rate was increased. Although the modulation frequency has increased to 5 Hz, the multiplicative term and modulation fundamental still overlap with the $1^{st}$ and $2^{nd}$ harmonics respectively. This demonstrates that the optimisation depends on the heart rate variability as well.

The fourth graph (FIG. 7d) illustrates the situation where the modulation frequency was set at 5.5 Hz. The multiplicative term overlapped the $2^{nd}$ harmonic.

The last graph (FIG. 7e) shows an optimised modulation frequency. Both the multiplicative term and the modulation fundamental were beyond the $3^{rd}$ harmonic region. This was done to cater for the variability of the heart rate.

Due to the proximity of the multiplicative term with the harmonics and the variability of the heart rate, the optimisation would result in a fairly narrow frequency band.

As mentioned earlier above, the modulation pressure can be adjusted according to the magnitude of the multiplicative term. The modulation pressure must be high enough to cause artificial pulsations in the venous blood system and yet not too strong as to affect the arterial system. The indicator of too great a pressure is the appearance of the multiplicative term in the frequency spectrum of the detected signal. Since the multiplicative term is an indication of the degree to which the underlying arterial system is being disturbed, it is important the term is minimised.

The graph shown in FIG. 8 illustrates the effect of modulation pressure and cuff to oximeter spacing on the level of the detected signal. Each of the curves plots the measured signal level against the modulation pressure, and the black dot indicates the point at which the multiplicative term becomes significant. By moving the modulation site closer to the site of measurement, the multiplicative term can be kept small, and the detected signal of a measurable level even with a relatively low pressure modulation. Typically the modulation pressure is set to result in approximately 0.1% variation in the DC level of the detected signal. The ideal balance between modulation pressure and modulation/measurement site spacing is represented by the space denoted "ideal design window". Typically a spacing of 30 to 50 mm is appropriate, depending on the pressure applied via the cuff. If the spacing is too small, the pulsations from the transducer will be coupled to the oximeter probe and cause a motion artefact in the received signal.

It is to be appreciated that in addition to the cuff and air pump arrangement, other ways of modulating pressure to generate a venous pulsatile signal are envisaged. This could for example be achieved by direct mechanical means or by applying electrical or thermal impulses to the site of modulation. Further, whilst the embodiment described applies positive pressure to the subject, a similar effect can be achieved by the application of negative pressure, for example by providing a vacuum pump to generate the perturbations to the system.

Whilst the oximeter probe and pressure transducer will generally be separate devices, they may also be formed as an integral device, provided that mechanical coupling between the transducer and the probe is avoided.

The specific embodiment described has employed the pulse oximeter probe in a transmission mode (in other words, the light passing through the digit, light source and sensor lying on opposite sides of the digit) but a probe operating in reflection mode could also be used. Since the veins lie close to the surface of the skin, if a reflection mode probe is used, the position of the probe could be used at a wide range of locations on the body, and is not limited to those regions where light is transmissible through the body tissue (digits, ear lobes etc).

In the event that both arterial and venous oxygen saturation are measured, this can be achieved simultaneously as described above. Alternatively, should the external pressure modulations disturb the calibration of the arterial oxygenation measurement, the measurement of these two quantities can be separated either physically (by measuring arterial and venous saturation at different sites) or temporally (e.g. by multiplexing the arterial and venous measurements over time). Where the measurement sites are separated physically, the probe may be either integrally formed, e.g. incorporating an arterial oximeter, and a venous oximeter and cuff, arranged to measure from two adjacent fingers, or may be formed of separate arterial and venous monitor devices.

A non-invasive method of determining venous oxygen content has been described which will allow accurate real time monitoring at lower risk to patients. This is of particular relevance during surgical recovery and management of therapy. A number of areas where the invention will find application are outlined below.

When patients are suffering from severe illness of either the cardiovascular system or the lungs their survival depends on the ability to optimise the delivery of oxygen to their tissues. Tailoring of oxygen delivery to match a patient's requirements is very difficult, even in an intensive care unit. It relies upon a combination of clinical assessment, laboratory blood tests, haemodynamic data and oximetry. These data are obtained from the insertion of catheters into the radial/femoral arteries and pulmonary artery and can take 1-2 hours to complete. The insertion of these lines carries a significant morbidity and mortality. The integration of the data needed to tailor the patient's oxygen delivery can take several hours to achieve. As such it is not suited to rapidly changing physiological situations. A rapidly applicable, non-invasive, measure of tissue oxygen delivery would benefit all critically ill patients in intensive care units. It would also be useful for patients in High Dependency Units and ordinary hospital wards. Perhaps its most useful potential application, however, would be in the resuscitation of patients. Non-invasive venous oximetry would allow resuscitation to be more focused; since the survival of patients suffering out-of-hospital cardiac arrest is <5%, this would be a great breakthrough. In addition, non-invasive venous oximetry would prove an invaluable aid to the safe transfer of critically ill patients between intensive care units. Indeed, studies performed by the inventors have shown that there is a close correlation between $SvO_2$ and cardiac output (CO), and therefore the method can also serve as a non-invasive indicator of Cardiac Output based on measurement of SvO2.

Cardio-Pulmonary Bypass (CPB) and Extracorporeal Membrance Oxygenation (ECMO) involve the temporary replacement of cardio-vascular and lung function by use of a pump-oxygenator. CPB is used in the operating theatre, whilst ECMO is used in the Intensive Care unit to support patients who are suffering from potentially reversible heart/lungs failure. Blood flow from the pump is non-pulsatile, and this means that conventional oxime try is ineffective. The ability to track oxygen delivery non-invasively with a device which does not rely on naturally pulsatile flow would have wide application. Since Coronary Artery Bypass Grafting (CABG) is the most commonly performed operation in the USA today this represents a significant potential application.

The diagnosis and monitoring of vascular disease and circulatory function will be enhanced by the availability of $SvO_2$ measurement. Elevated $SvO_2$ measures at rest may indicate reduced tissue perfusion due to impaired blood flow. Monitoring venous oxygen saturation will therefore allow the severity of injury and functional compromise resulting from trauma to be examined more easily. Depressed $SvO_2$ measures may suggest tissue dysfunction and monitoring will allow judgements to be made about the viability of tissue during trauma or disease.

As the $PaO_2$ drops below about 40 Torr, even small changes in the partial pressure of inspired oxygen result in large decreases in $SaO_2$. $SvO_2$ measurement will enhance the monitoring of hypoxia in a range of conditions. Physical training evokes peripheral adaptations to allow for effective utilisation of the increase in $O_2$ delivery resulting in higher $O_2$ diffusional conductance in muscle. The effect of endurance training can be observed as a greater capillary density allowing for a longer transit time at a given blood flow and also a higher a $\overline{v}O_2$ difference. The invention would be a valuable tool in performing exercise/stress tests and examining the effects of heat and cold, micro-gravity and dehydration. It would also support numerous other medical and physiological research themes.

The invention claimed is:

1. A method of non-invasively measuring venous oxygen saturation, comprising
   applying a pressure transducer at a first site on a body having venous and arterial systems,
   applying a drive signal to the pressure transducer at a predetermined frequency, to cause a series of pulsations of a predetermined magnitude in the venous blood volume in the vicinity of said first site, the magnitude of the pulsations being adjusted such that the arterial system is minimally disturbed,
   applying an oximeter device at a second site on the body,
   measuring output signals received from said oximeter device, said output signals containing a component representative of the modulation of venous blood volume due to said pulsations,
   deriving a measure of venous oxygen saturation from the frequency response of said output signals.

2. A method according to claim 1 wherein the relationship between the distance between the first and second sites on the one hand, and the magnitude of the pulsations on the other hand, is such that a multiplicative term in the frequency spectrum of the measured signals, indicative of a disturbance to the arterial system, is minimised.

3. A method according to claim 2 wherein the magnitude of the pulsations is determined by progressively increasing the pulsation magnitude and observing a frequency response of the output signals, the appearance of a multiplicative term in the frequency spectrum being indicative of the maximum permissible magnitude having been reached.

4. A method according to claim 3, wherein, upon reaching the point where said multiplicative term appears, the pulsation magnitude is subsequently reduced to a point where the multiplicative term becomes insignificant.

5. A method according to claim 1 wherein the frequency of the drive signal is chosen such that the pulsations are distinguishable from the heart rate.

6. A method according to claim 5 wherein the frequency of the drive signal is determined iteratively on the basis of a real time measurement of the heart rate.

7. A method according to claim 1 wherein the relationship between the frequency $\omega_m$ of the pulsations caused by said drive signal and the heart rate $\omega_{HR}$ is chosen to comply with the following conditions:

$$\omega_m \neq n(\omega_{HR} \pm \Delta\omega_{HR})$$

and $$\omega_m \pm (\omega_{HR} \pm \Delta\omega_{HR}) \neq n(\omega_{HR} \pm \Delta\omega_{HR})$$

where n>1.

8. A method according to claim 1 wherein the magnitude of the pulsations is adjusted such as to cause a variation of less than 1% in the DC level of the output signals received from the oximeter device.

9. A method according to claim 8 wherein the magnitude of the pulsations is adjusted such as to cause a variation of approximately 0.1% in the DC level of the output signals received from the oximeter device.

10. A method according to claim 1 wherein the oximeter is placed on a digit and a further pressure transducer is placed away from a distal end of a limb, and arranged to occlude the supply of blood to and from said limb, and the measurement is performed during the period of occlusion.

11. A method according to claim 1, further including a calibration step, during which the spacing between the first and second sites is varied while the pulsation magnitude is held constant, in order to derive an optimum spacing.

12. A method according to claim 11, wherein the calibration step includes a further step of varying the pulsation magnitude while the spacing of the first and second sites is held constant.

13. A method according to claim 1, wherein a measure of arterial oxygen saturation is derived from the frequency response of said output signals, and the difference is levels of said arterial and venous oxygen saturation is representative of tissue oxygen consumption.

14. Apparatus for non-invasively measuring venous oxygen saturation comprising:
   a pressure transducer for applying a series of pulsations to a first site on a body having venous and arterial systems,
   a pulse oximeter,
   control means for controlling the frequency and/or magnitude of said pulsations, such that the venous blood volume is modulated, the control means being operable to adjust the magnitude of the pulsations such that the arterial system is minimally disturbed,
   signal processing means for extracting a value for venous oxygen saturation from signals received from said oximeter, said signals containing a component representative of a modulation of venous blood volume due to said pulsations.

15. A device according to claim 14 wherein said control means operates to control the relationship between the frequency $\omega_m$ of the pulsations caused by said drive signal and the heart rate $\omega_{HR}$ according to the following conditions:

$$\omega_m \neq n(\omega_{HR} \pm \Delta\omega_{HR})$$

and $$\omega_m \pm (\omega_{HR} \pm \Delta\omega_{HR}) \neq n(\omega_{HR} \pm \Delta\omega_{HR})$$

where n>1.

16. A device according to claim 14 wherein the pressure transducer comprises an inflatable digit cuff supplied with air from an air pump.

17. A device according to claim 16 wherein said pressure transducer and said pulse oximeter are formed as an integral device.

18. A method of non-invasively measuring venous oxygen saturation, comprising
applying a pressure transducer at a first site on a body,
applying a drive signal to the pressure transducer at a predetermined frequency, to cause a series of pulsations of a predetermined magnitude in the venous blood volume in the vicinity of said first site,
applying an oximeter device at a second site on the body,
measuring output signals received from said oximeter device, said output signals containing a component representative of the modulation of venous blood volume due to said pulsations, deriving a measure of venous oxygen saturation from the frequency response of said output signals,
wherein the magnitude of the pulsations is determined by progressively increasing the pulsation magnitude and observing a frequency spectrum of the measured output signals, the appearance of a multiplicative term in the frequency spectrum, indicative of a disturbance to the arterial system, indicating that the maximum permissible magnitude has been reached and wherein, upon reaching the point where said multiplicative term appears, the pulsation magnitude is subsequently reduced to a point where the multiplicative term becomes insignificant.

* * * * *